United States Patent [19]

Lawrence

[11] Patent Number: 4,926,882
[45] Date of Patent: May 22, 1990

[54] TRANSPARENT SHIELDING DEVICE FOR USE WITH AUTOPSY SAW

[76] Inventor: Sharon K. Lawrence, 789 Bayard St., Teaneck, N.J. 07666

[21] Appl. No.: 240,694

[22] Filed: Sep. 6, 1988

[51] Int. Cl.$^5$ ............................................. A61F 13/00
[52] U.S. Cl. ..................................... 128/850; 128/853
[58] Field of Search ............... 128/849, 850, 851, 852, 128/853, 854, 855, 856, 857, 873; 2/D7, 171, 171.1, 171.2, 171.3, 171.4, 171.5

[56] References Cited

U.S. PATENT DOCUMENTS

| | | | |
|---|---|---|---|
| 1,148,902 | 8/1915 | Jacobs | 2/6 |
| 1,398,165 | 11/1921 | Whiteside | 2/171 |
| 2,294,593 | 9/1942 | Bailey | 128/857 |
| 3,423,763 | 1/1969 | Schwartz | 2/171 |
| 3,951,160 | 4/1976 | Nitu | 2/424 |
| 4,122,848 | 10/1978 | Carpel | 128/849 |
| 4,275,719 | 6/1981 | Mayer | 128/849 |
| 4,367,728 | 1/1983 | Mutke | 128/853 |
| 4,457,026 | 7/1984 | Morris | 128/851 |
| 4,485,806 | 12/1984 | Akers | 128/873 |
| 4,605,000 | 8/1986 | Anguita | 2/171.2 |

Primary Examiner—Robert A. Hafer
Assistant Examiner—Michael Brown
Attorney, Agent, or Firm—Siegmar Silber

[57] ABSTRACT

The invention discloses a protective device for use during autopsy by a prosector operating with handheld instruments. The autopsy subject is covered by a transparent dissection chamber-forming device which is attached to the draped about the body of the subject. By attaching the device to the body of the subject the dissection site is isolated from the prosector and his support staff. The device provides an instrument port through which the handheld instrument can be partially inserted and further the device provides for sealing against the instrument. In addition to the device, a method of protecting autopsy room staff is also disclosed. Through the device and the associated method, the prosector is enabled to use, with an unobstructed view of the autopsy subject, handheld instruments while the effluent from the dissection of the autopsy subject is restricted within the sealed dissection chamber. The autopsy room staff is thus protected from infection.

9 Claims, 5 Drawing Sheets

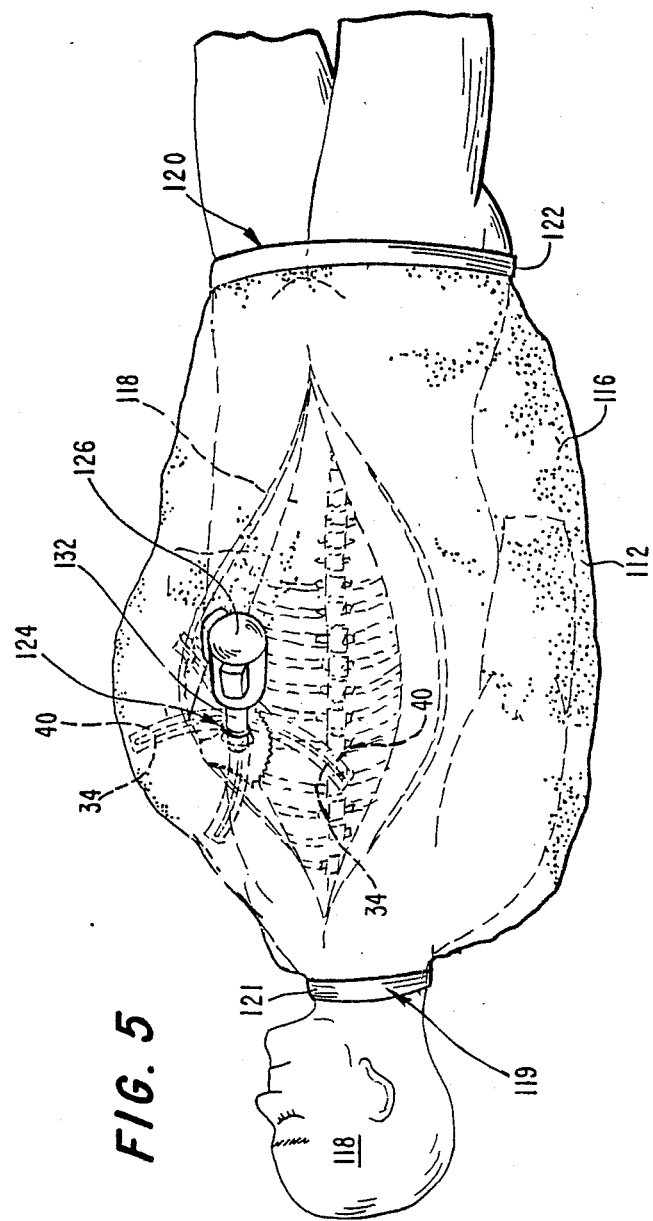

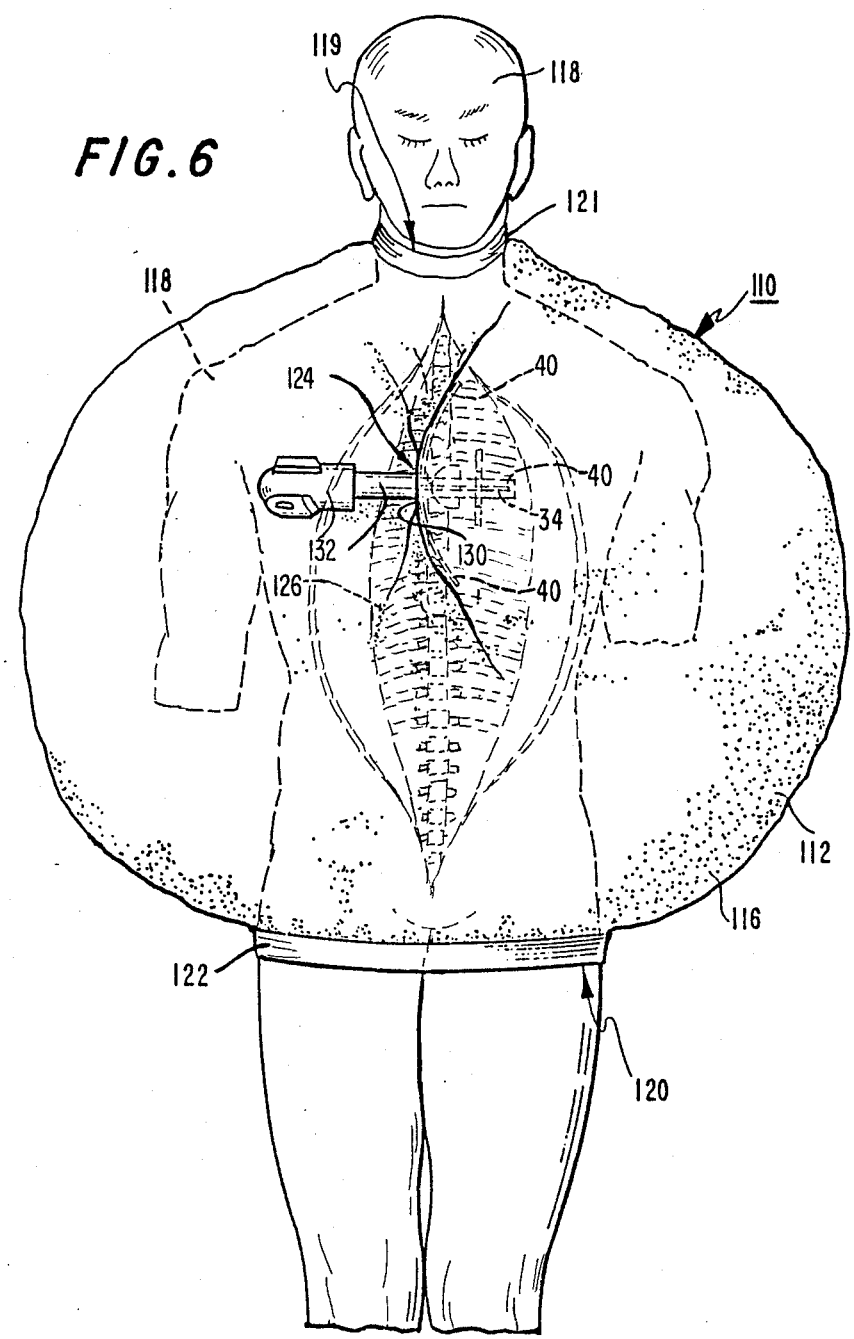

TRANSPARENT SHIELDING DEVICE FOR USE WITH AUTOPSY SAW

BACKGROUND OF THE INVENTION

1. Field of the Invention

This invention relates to disposable protective shielding for autopsy room use, and more particularly to a specially designed disposable transparent dissection chambers for use during brain removal and spinal cord removal procedures.

2. Information Disclosure Statement

In present-day practice, medical and technical personnel are exposed to risk of infection during standard autopsy room procedures. In the autopsy room setting less emphasis is seemingly placed on staff safety than in other segments of hospital service. This probably stems from the removal of standards of care to the patient (such as prevails under the sterile operating room conditions) and the emphasis on production requirements by autopsy staff. Such staff is regularly exposed to tuberculosis; viral infections, including hepatitis, acquired immune deficiency syndrome (AIDS), and a variety of herpes viruses; bacterial infections, including those from various strains of salmonellae, clostridia, staphylococci, and streptococci; and, parasitic diseases, such as leptospirosis and hydatidosis.

With the advent of AIDS cases, more emphasis has been placed on staff safety. As will be seen from the details of the disclosure at hand, especial attention is drawn to brain removal and spinal cord removal procedures. In these procedures, perhaps more so than in others, autopsy saws are used in a manner that produces airborne particulates and, from body fluids, splashes and aerosols.

In preparing for this application, a pre-examination patentability search was obtained with the search being conducted in Class 128, subclasses 132R and 132D. The search uncovered the following patents:

| U.S. Pat. No. | Inventor (Assignee) | Date of Issue |
| --- | --- | --- |
| 4,607,631 | Haussen (Moinlycke AB) | 8/26/86 |
| 4,457,026 | Morris (Surgikos) | 7/3/84 |
| 3,800,790 | Collins (The Kendall Co.) | 4/2/74 |
| 3,797,484 | Ericson (C. R. Bard, Inc.) | 3/19/74 |
| 2,305,289 | Coburg | 12/15/42 |

Hansen teaches in U.S. Pat. No. 4,607,631 a surgical sheet designed to prevent access to the surgeon to non-sterile portions of the patient, which portions have not been "prepped." Additionally, an access hole is taught which has no functional role other than to hold the surgical sheet snugly against the patient. The patent to Morris, U.S. Pat. No. 4,457,026, is a surgical drape for eye, ear, nose and throat (EENT) procedures and was selected as it shows a draping procedure. Generally, this teaches a draped sheet arrangement about the head with the sheeting having a completely closed end without using clamps or tapes. Turning now to Collins, U.S. Pat. No. 3,800,790, and to Ericson, U.S. Pat. No. 3,797,484, two different versions of surgical drapes of the cystoscopy type are taught. Each has different means for handling liquid effluents from the fenestration opening or instruments. One sheeting incorporates a filter retaining solids from such effluents. The Coburg patent was included as being of interest only. Accordingly, none of the items uncovered on search were considered as teaching the disclosure at hand and otherwise no relevant patents were uncovered on search.

In further preparation for this application a review of the marketplace was conducted. Applicant was not able to obtain a transparent shielding device adapted for use in conjunction with an autopsy saw.

SUMMARY OF THE INVENTION

The invention discloses various protective devices for use in an autopsy room. The device is attached to the subject and provides surrounding the portion to be dissected, a sealed dissection chamber. An autopsy instrument port is provided which enables the prosector to insert a tool, such as an oscillating autopsy saw, partly into the chamber, yet manipulate the tool without interference from the protective device. To facilitate use of the protective device supports are provided for preventing the draping of the protective device onto the site being dissected. In the disclosure which follows two modes of the invention are disclosed. The first being the protective device for use during brain removal and the second a protective device for use during spinal cord removal. Both embodiments are used in conjunction with an oscillating autopsy saw. Normally when such saws are used, body fluids are splashed about and aerosols are formed. Additionally, particulate matter, including bone chips frequently become airborne.

The art to date has not provided a mechanism for safeguarding autopsy room staff from impingement by such foreign matter and thus such staff has been subjected to a hazardous environment supportive of infections. Consequently the disclosed device has the following objects and features.

It is an object of the present invention to provide a transparent shield for use during an autopsy by a prosector operating with hand-held instruments.

It is a further object of the invention that the protective device be easily and efficiently installed upon the subject and, while providing shielding not interfere with the work of dissection.

It is a yet further object of the invention to provide a transparent shield which protects the autopsy room staff from impingement from body fluids, aerosols and particulate matter originating from the subject being dissected.

It is yet another object of the present invention to provide a protective sealing device for use during brain removal and spinal cord removal procedures.

It is a feature of the present invention to provide an instrument port in the protective seal, which port seals against the shank of the hand-held instrument.

It is a further feature of the invention to seal the protective seal against the subject without substantial delay of the autopsy procedures.

Other objects and features of the invention will become apparent upon the reading of the detailed description of the preferred embodiments which follow.

BRIEF DESCRIPTION OF THE DRAWINGS

In the figures which follow identical parts shown on various views bear the same reference numbers.

FIG. 5 is a perspective view of the second embodiment of the present invention showing a disposable transparent shield for spinal cord removal procedure; and, FIG. 6 is a top elevational view of the invention shown in FIG. 5.

DESCRIPTION OF THE PREFERRED EMBODIMENT

Figure 1:
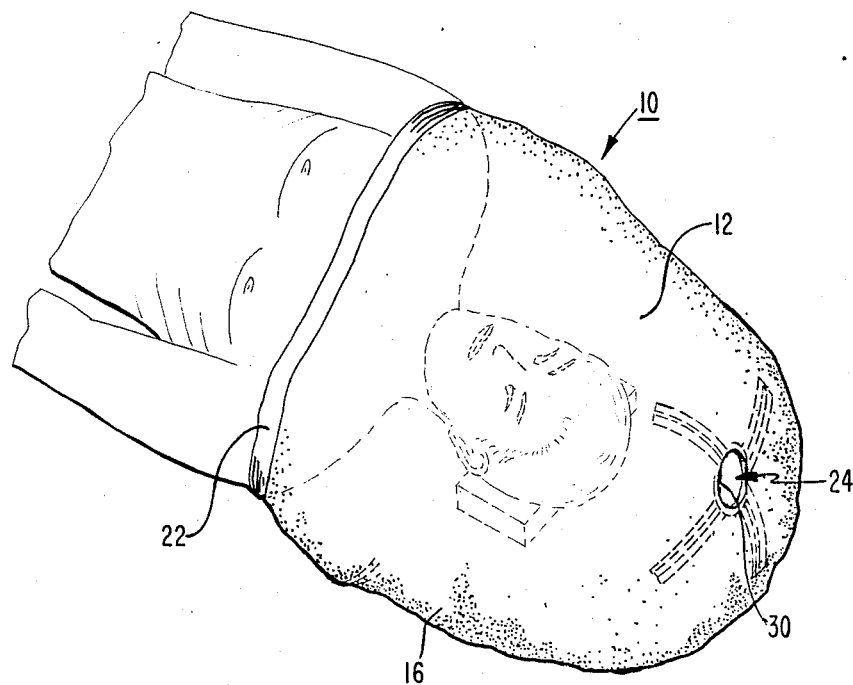
FIG. 1 is a perspective view of the first embodiment of the present invention showing a disposable transparent shield for brain removal procedure.
Figure 3:
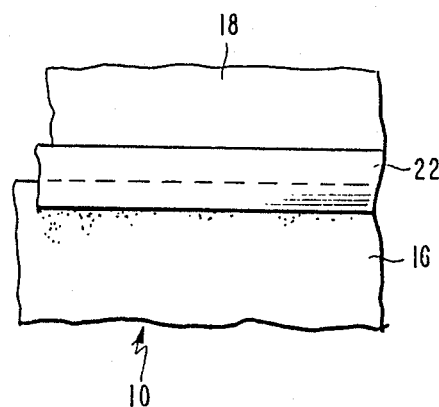
FIG. 3 is a detailed view of the attachment band of FIG. 2 by which the transparent shield is attached to the subject of the autopsy.
Figure 2:
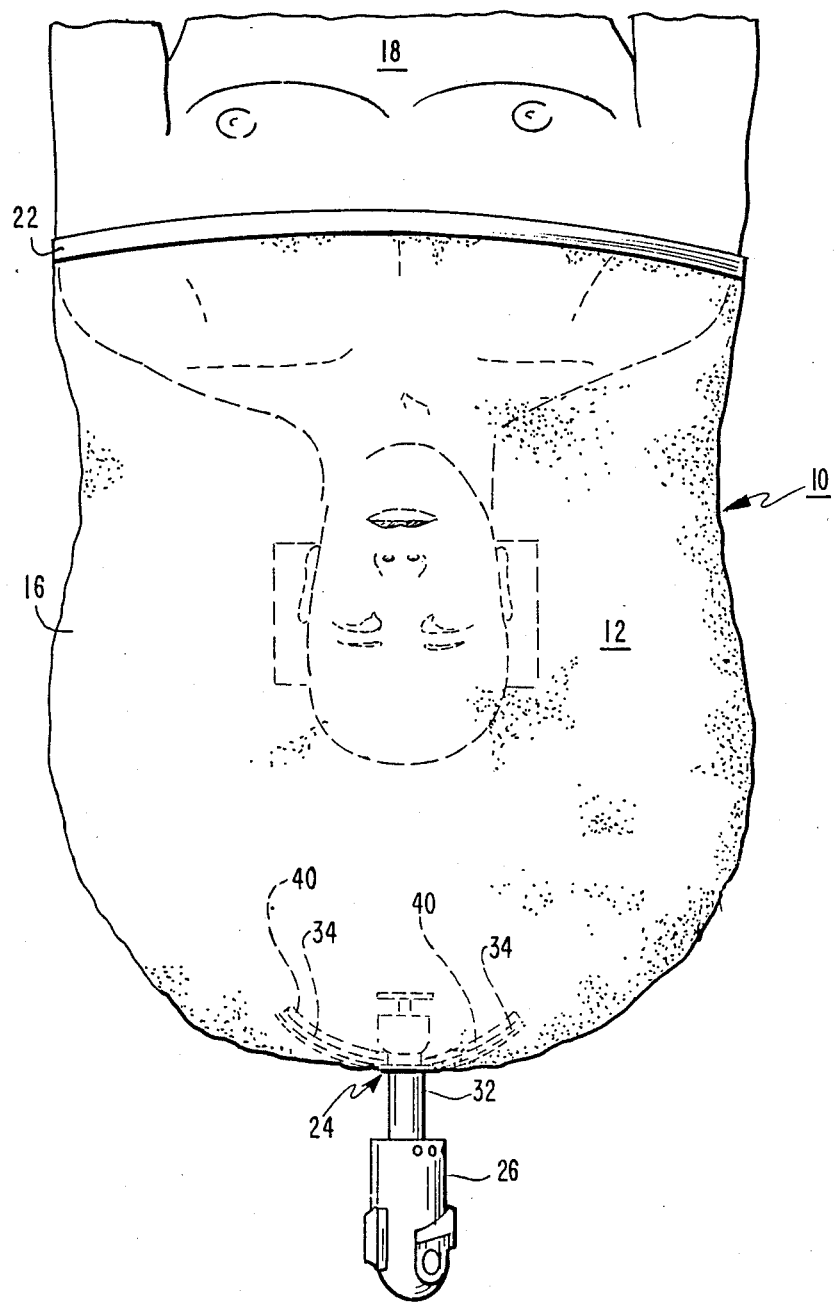
FIG. 2 is a top elevational view of the invention shown in FIG. 1.
Figure 4:
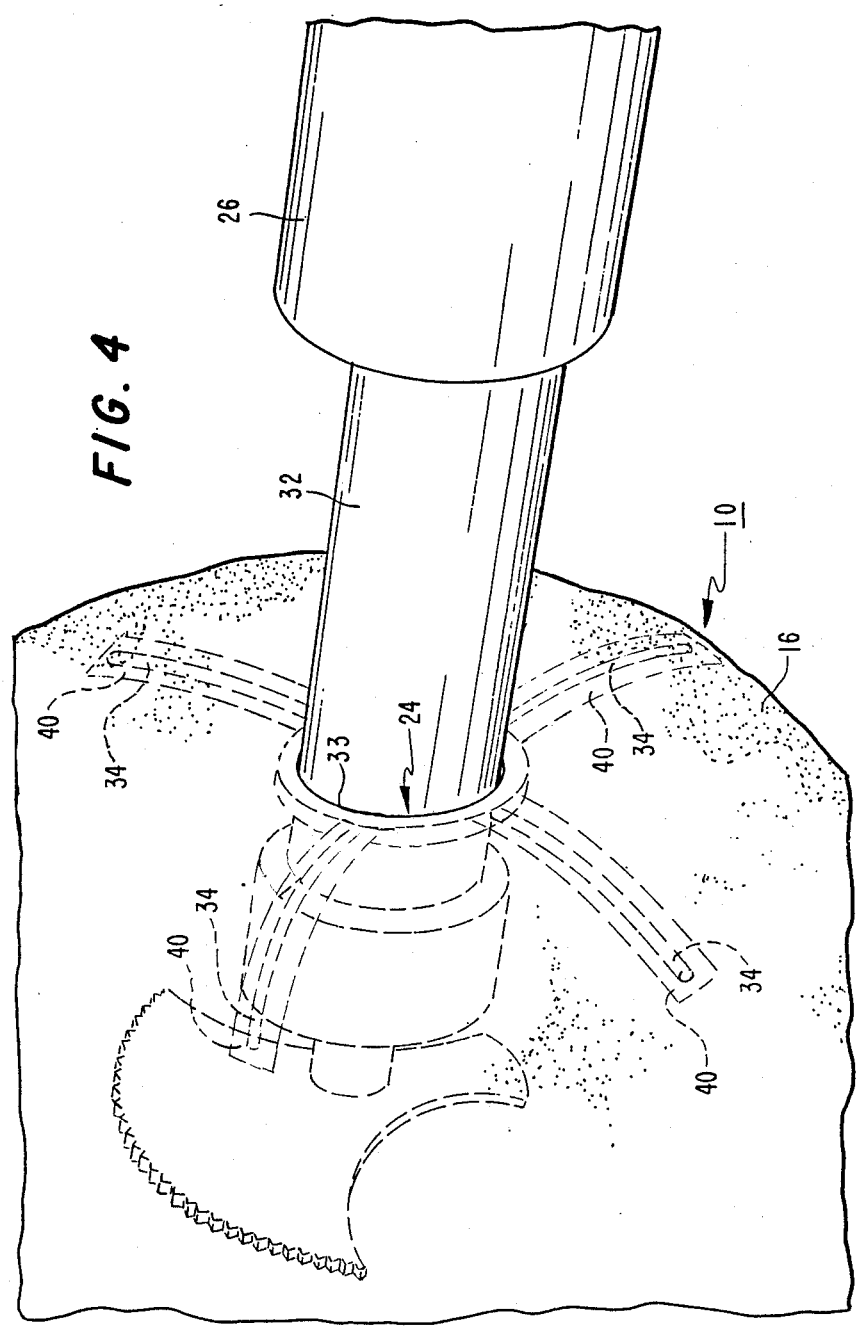
FIG. 4 is a detailed view of FIG. 2 of the instrument port, an oscillating autopsy saw mounted therein, and the sealing of the port to the shank of the saw.

In the embodiment shown in FIGS. 1 through 4, a protective device or a transparent dissection chamber is illustrated and is referred to generally by the reference numeral 10. The dissection chamber 10 is constructed with a transparent, sheet-like body 12 having an inside face or inner surface 14 and an outside face or outer surface 16. The first embodiment is proportioned so that the device 10 fits the subject of the autopsy 18 during the brain removal procedure. The sheet-like body 12 has a large opening 20 with an attachment means or tape band 22 adapted to seal the torso of the subject 18 and the opening 20 together. Although an attachment means 22 is shown as a tape construction those skilled in the art could devise other attachment means including but not limited to drawstring, elasticized cuff, and adhesive coating of the inner surface 14 adjacent opening 20. With the attachment seal 22 completed, the dissection chamber 10 is erected about the head of the subject. At the end opposite the large opening 20, the protective device 10 is structured to include an instrument port 24 and, in the embodiment, dimensioned to house an oscillating autopsy saw 26. While a variety of saws are available, probably the most commonly used is the Stryker Autopsy Saw (Stryker Surgical Co., Kalamazoo, Mich. 49001) which cuts bone without cutting adjacent soft tissue. An instrument seal 28 seals the edges 30 of the port 24 to the shank 32 of saw 26. Arrayed about the body 12, one or more support ribs 34 are inserted into pockets 40. Although the pockets are shown Arrayed on the outer surface 16, the rib-and-pocket arrangement would function equally well if mounted on the inner surface 14.

Referring now to FIGS. 5 and 6, a second embodiment is shown and is referred to generally by the reference numeral 110. In describing the second embodiment an analogy is drawn to the previously described embodiment. As an aid to the reader, similar parts in the second embodiment to those in the first embodiment are afforded reference numbers "100" units higher Thus, the sheet-like body 12 of the first embodiment has an analog in sheet-like body 112 of the second embodiment. The dissection chamber 110 is constructed with a transparent, sheet-like or tubular body 112 having an inside face or inner surface 114 and an outside face or outer surface 116. The first embodiment is proportioned so that the device 110 fits the subject of the autopsy 118 during the spinal cord removal procedure. The sheet-like body 112 has a large opening 120 with an attachment means or tape band 122 adapted to seal the hips of the subject 118 and the opening 120 together. Analogous to attachment means 22, although attachment means 122 is shown as a tape construction, those skilled in the art could device other attachment means including, but not limited to, drawstring, elasticized cuff, and adhesive coating of the inner surface 114 adjacent opening 120. The sheet-like body 112 has a small opening 119 with an attachment means or tape band 121 adapted to seal the neck of the subject 118 and the opening 121 together. With the attachment seals 121 and 122 completed, the dissection chamber 110 is erected about the spinal column of the subject. At a point medial the openings 119 and 120, the protective device 110 is structured to include an instrument port 124 and, to house an oscillating autopsy saw 126. An instrument seal 128 seals the edges 130 of the port 124 to the shank 132 of saw 126.

In the preceeding discussion, the autopsy saw and protective shielding devices for brain removal and spinal cord removal procedures, respectively, are discussed separately. However, it is within the scope of this invention to combine the shield and saw as an operative assemblage.

In operation, the protective device is first discussed in terms of general applications. As will become apparent hereinbelow the protective device is designed primarily for use with the autopsy saw. Although so designed, the instrument ports are multifunctional in that the posts may accommodate any instrument with a handle at one end, a shank portion against which to seal the edge of the port, and an operating end to extend into the dissection chamber. To optimize the protective aspect of the shield, the preparatory steps that are less hazardous, than for example using the autopsy saw, are performed prior to erecting the dissection chamber. The extent of the dissection to be performed by the prosector is next established, and the autopsy room staff isolates this region of the subject by attaching the shield to the subject. In the embodiments shown in one case, the cranial area is isolated, and in the other, the spinal area is isolated. Thereafter the protective device with suitable geometry is selected and attached to the subject. The attachment is carried out in a manner which provides ample room for manipulation of the instrument. Next the instrument is sealed to the port adjacent the dissection site. Supports are inserted to maintain the shield away from the dissection site.

The application of the shielding is now discussed in relation to the brain removal procedure. In this autopsy procedure, numerous steps are performed prior to requiring the use of the autopsy saw. While these preliminary procedures present some level of hazard, the hazardous operations are of a different level of magnitude when the autopsy saw is then used. Typically, in using the autopsy saw, blood and other body fluids are splashed from the site of the cutting operation. Further danger is created by the fluids being worked by the high-frequency oscillating blade to form aerosols; and the solids (such as bone), to form airborne particulates. Among the preliminary steps, not part of the method of this invention is the preparing of formalin to receive the removed brain and the reflecting of the scalp to expose the skull. Thereafter, the following steps are followed:

a. attaching the protective shield or body to the subject by the following substep:
   1. adhering by tape or equivalent means to the torso of the subject thereby sealing the large opening described above, to the subject;
b. draping the remaining portion of the protective shield so that the instrument port is convenient to the cranial area;

c. inserting the autopsy saw through the instrument port so that the oscillating blade is adjacent the cranial area; within the dissection chamber; and, d. sealing the opening of the instrument port to the shank of the autopsy saw; and, e. supporting the dissection chamber by aligning the supporting members as required by the geometry of the subject;

f. cutting the bony portion of the skull in the prescribed manner for facilitating removal of the brain; and, g. retaining the products of the cutting within the dissection chamber.

Next, the application of the shielding is discussed in relation to the spinal cord removal procedure.

Likewise in this autopsy procedure, numerous steps are performed prior to requiring the use of the autopsy saw. While these preliminary procedures present some level of hazard, the hazardous operations are of a different level of magnitude when the autopsy saw is then used. Typically, in using the autopsy saw, blood and other body fluids are splashed from the site of the cutting operation. Further danger is created by the fluids being worked by the high-frequency oscillating blade to form aerosols; and the solids (such as bone), to form airborne particulates. Among the preliminary steps, not part of the method of this invention is the preparing of formalin to receive the removed spinal cord and the incising the anterior lamina to expose the spinal column. Thereafter, the following steps are follows:

a. attaching the protective shield or body to the subject by the following substep:

1. adhering by tape or equivalent means to the hips of the subject thereby sealing the large opening, described above, to the subject;

2. adhering by tape or equivalent means to the neck of the subject thereby sealing the small opening, described above, to the subject;

b. draping the remaining portion of the protective shield so that the instrument port is convenient to the cranial area;

c. inserting the autopsy saw through the instrument port so that the oscillating blade is adjacent the cranial area; within the dissection chamber;

d. sealing the opening of the instrument port to the shank of the autopsy saw;

e. supporting the dissection chamber by aligning the supporting members as required by the geometry of the subject;

f. cutting the bony portion of the skull in the prescribed manner for facilitating removal of the brain; and, g. retaining the products of the cutting within the dissection chamber.

What is claimed is:

1. A protective shield and saw assembly for use during an autopsy by a prosector operating upon a subject comprising, in combination:

a transparent shield for attachment to and for draping about said subject, said shield having an inside and an outside face and, when said shield is draped about said subject, the inside face is adjacent said subject;

one or more attachment means for sealing said body to the subject, said attachment means for isolating the portion of said subject to be dissected and for defining a sealed dissection chamber thereabout;

at least one autopsy instrument port means for inserting an oscillating autopsy saw partly into said chamber with the handle thereof adjacent the outside face of said body; and, an instrument seal means for sealing said port means to said saw;

an oscillating autopsy saw mounted with the blade portion in the dissection chamber and the instrument seal means sealed to the shank of the saw;

whereby the prosector, when the protective shield and saw assembly is employed, is enabled to use with an unobstructed view thereof, said oscillating autopsy saw upon said subject while restricting the effluent from the dissection of the subject to said sealed dissection chamber and thereby protecting the prosector from infection.

2. A protective shield and saw assembly as described in claim 1 wherein said shield is bag-shaped with the mouth thereof adapted for attachment to the torso of the subject forming a dissection chamber adjacent the head of the subject for use during a brain removal procedure.

3. A protective shield and saw assembly as described in claim 2 wherein said bag-shaped body further comprises chamber support means for holding the chamber wall away from the dissection site, said chamber support means supporting said transparent shield proximate said instrument port.

4. A protective shield and saw assembly as described in claim 1 wherein said shield is tubular having two open ends with one open end thereof adapted for attachment to the neck of the subject and with the other open end thereof adapted for attachment to the hips of the subject forming a dissection chamber adjacent the spine of the subject for use during a spinal cord removal procedure.

5. A protective shield and saw assembly as described in claim 4 wherein said bag-shaped body further comprises chamber support means for holding the chamber wall away from the dissection site, said chamber support means supporting said transparent shield proximate said instrument port.

6. A method of protecting autopsy room staff during an autopsy by a prosector operating with hand-held instruments upon a subject comprising the following steps:

a. draping a transparent sheet-like body about said subject, said sheet-like body having at least one instrument port therethrough and having an inside and an outside face which, when said sheet-like body is draped about said subject, the inside face of said sheet-like body is adjacent said subject, said sheet like body being tubular with two open ends with one open end thereof adapted for attachment to the neck of the subject and with the other open end thereof adapted for attachment to the hips of the subject forming a dissection chamber adjacent the spine of the subject for use during a spinal cored removal procedure;

b. sealing said sheet-like body to the subject;

c. isolating the portion of said subject to be dissected and defining a sealed dissection chamber thereabout;

d. at an autopsy instrument port, inserting an oscillating autopsy saw partly into said chamber with the handle thereof adjacent the outside face of said body; and, e. sealing said port to said instrument;

whereby the prosector, when the protective device is employed, is enabled by the method to use, with an unobstructed view thereof, said instrument upon said subject while restricting the effluent from the dissection of the subject to said sealed dissection chamber and thereby protecting the said autopsy room staff from infection.

7. A method as described in claim 6 further comprising the step of: holding the chamber wall away from the dissection site by a chamber support means.

8. A method as described in claim 7 further comprising the steps of: cutting through the spinal column to expose the spinal cord; and, retaining the effluent of the spinal cord removal procedure within the dissection chamber.

9. A method of protecting autopsy room staff during autopsy by a prosector operating with hand-held instruments upon a subject comprising the following steps:
 a. draping a transparent sheet-like body about said subject, said sheet-like body having at least one instrument port therethrough and having an inside and an outside face which, when said sheet-like body is draped about said subject, the inside face of said sheet-like body is adjacent said subject, said sheet like body being bag-shaped with the mouth thereof adapted for attachment to the torso of the subject and adapted for forming a dissection chamber adjacent the head of the subject for use during a brain removal procedure;
 b. sealing said sheet-like body to the subject;
 c. isolating the portion of said subject to be dissected and defining a sealed dissection chamber thereabout;
 d. at an autopsy instrument port, inserting an oscillating autopsy saw partly into said chamber with the handle thereof adjacent the outside face of said body; and,
 e. sealing said port to said instrument;
 f. holding the chamber wall away from the dissection site by a chamber support means;
 g. cutting through the cranial bones to expose the brain; and,
 h. retaining the effluent of the brain removal procedure within the dissection chamber;
whereby the prosector, when the protective device is employed, is enabled by the method to use, with an unobstructed view thereof, said instrument upon said subject while restricting the effluent from the dissection of the subject to said sealed dissection chamber and thereby protecting the said autopsy room staff from infection.

* * * * *